(12) United States Patent
Cole et al.

(10) Patent No.: US 10,099,027 B2
(45) Date of Patent: Oct. 16, 2018

(54) ORAL SUCTION DEVICE

(71) Applicant: COLE Research & Design, Inc., Jackson, MS (US)

(72) Inventors: Jeptha N. Cole, Jackson, MS (US); Nina E. McLain, Philadelphia, MS (US)

(73) Assignee: Cole Research & Design, Jackson, MS (US)

( * ) Notice: Subject to any disclaimer, the term of this patent is extended or adjusted under 35 U.S.C. 154(b) by 529 days.

(21) Appl. No.: 14/603,634

(22) Filed: Jan. 23, 2015

(65) Prior Publication Data

US 2015/0209535 A1    Jul. 30, 2015

Related U.S. Application Data

(60) Provisional application No. 62/057,067, filed on Sep. 29, 2014, provisional application No. 61/931,463, filed on Jan. 24, 2014.

(51) Int. Cl.
*A61M 16/04*    (2006.01)
*A61M 25/00*    (2006.01)
(Continued)

(52) U.S. Cl.
CPC ........ *A61M 16/0463* (2013.01); *A61M 16/04* (2013.01); *A61M 16/0475* (2014.02);
(Continued)

(58) Field of Classification Search
CPC .. A61M 16/00; A61M 16/0003; A61M 16/04; A61M 16/0402; A61M 16/0409; A61M 16/0411; A61M 16/0415; A61M 16/0422; A61M 16/0427; A61M 16/0429; A61M 16/0443; A61M 16/0445; A61M 16/0454; A61M 16/0461; A61M 16/0463; A61M 16/0465; A61M 16/0475; A61M 16/0477; A61M 16/0479; A61M 16/0481;
(Continued)

(56) References Cited

U.S. PATENT DOCUMENTS 3,101,543 A * 8/1963 Baughan .............. A61C 17/043
                                                                433/94
3,324,855 A * 6/1967 Heimlich .............. A61B 17/02
                                                                401/133
(Continued)

FOREIGN PATENT DOCUMENTS

EP    0 355 199    2/1990
EP    0 578 121    1/1994
(Continued)

OTHER PUBLICATIONS

Maldonado-Codina, C. et al., "Hydrogel lenses—materials and manufacture: a review", Optometry in Practice, vol. 4, pp. 101-115, (2003).
(Continued)

*Primary Examiner* — Colin W Stuart
(74) *Attorney, Agent, or Firm* — Evan Law Group LLC

(57) ABSTRACT

An oral suction device includes a suction catheter having a suction portion at a first end, a shell surrounding the suction portion, and a suction tubing connector on a second end opposite the first end. The shell includes a hydrogel.

25 Claims, 8 Drawing Sheets

(51) Int. Cl.
  *A61B 10/00* (2006.01)
  *A61M 1/00* (2006.01)
  *A61B 7/02* (2006.01)
  *A61M 16/08* (2006.01)

(52) U.S. Cl.
  CPC ......... *A61M 16/0477* (2014.02); *A61B 7/023* (2013.01); *A61B 10/0051* (2013.01); *A61M 1/008* (2013.01); *A61M 1/0039* (2013.01); *A61M 1/0064* (2013.01); *A61M 16/0816* (2013.01); *A61M 2025/0057* (2013.01); *A61M 2210/0625* (2013.01); *A61M 2230/50* (2013.01)

(58) Field of Classification Search
  CPC ............. A61M 16/0484; A61M 25/00; A61M 25/0012; A61M 25/0014; A61M 25/0015; A61M 25/0021; A61M 25/0026; A61M 25/0029; A61M 25/003; A61M 25/0043; A61M 25/0045; A61M 25/0071; A61M 25/0108; A61M 25/0111; A61M 2025/0004; A61M 2025/0006; A61M 2025/0018; A61M 2025/0024; A61M 2025/0031; A61M 2025/0039; A61M 2025/0037; A61M 2025/0046; A61M 2025/0056; A61M 2025/0057; A61M 2025/0062; A61M 1/0039; A61M 1/008; A61M 1/0064; A61B 10/0045; A61B 10/0051; A61F 13/36; A61F 13/38; A61F 11/006; A61F 35/006
  USPC .................................................. 600/573–584
  See application file for complete search history.

(56) References Cited

U.S. PATENT DOCUMENTS

| | | |
|---|---|---|
| 4,988,342 A | 1/1991 | Herweck et al. |
| 4,995,386 A | 2/1991 | Ng |
| 5,000,175 A | 3/1991 | Pue |
| 5,082,007 A | 1/1992 | Adell |
| 5,158,569 A | 10/1992 | Strickland et al. |
| 5,160,319 A | 11/1992 | Emery et al. |
| 5,215,522 A | 6/1993 | Page et al. |
| 5,253,658 A | 10/1993 | King |
| 5,254,086 A | 10/1993 | Palmer et al. |
| 5,257,620 A | 11/1993 | Schermerhorn |
| 5,277,177 A | 1/1994 | Page et al. |
| 5,279,549 A | 1/1994 | Ranford |
| 5,330,424 A | 7/1994 | Palmer et al. |
| 5,349,950 A | 9/1994 | Ulrich et al. |
| 5,361,753 A | 11/1994 | Pothmann et al. |
| 5,368,017 A | 11/1994 | Sorenson et al. |
| 5,397,299 A | 3/1995 | Karwoski et al. |
| 5,401,262 A | 3/1995 | Karwoski et al. |
| 5,419,769 A | 5/1995 | Devlin et al. |
| 5,456,689 A | 10/1995 | Kresch et al. |
| 5,460,613 A | 10/1995 | Ulrich et al. |
| 5,487,731 A | 1/1996 | Denton |
| 5,490,503 A | 2/1996 | Hollister |
| 5,496,268 A | 3/1996 | Perla |
| 5,507,279 A | 4/1996 | Fortune et al. |
| 5,527,331 A | 6/1996 | Kresch et al. |
| 5,551,421 A | 9/1996 | Noureldin et al. |
| 5,562,077 A | 10/1996 | Schultz |
| 5,591,130 A | 1/1997 | Denton |
| 5,598,840 A | 2/1997 | Iund et al. |
| 5,605,149 A | 2/1997 | Warters |
| 5,611,336 A | 3/1997 | Page et al. |
| RE35,595 E | 8/1997 | Six |
| 5,655,258 A | 8/1997 | Heintz |
| 5,667,500 A | 9/1997 | Palmer et al. |
| 5,720,078 A | 2/1998 | Heintz |
| 5,741,272 A | 4/1998 | Kuhne |
| 5,743,894 A | 4/1998 | Swisher |
| 5,765,557 A | 6/1998 | Warters |
| 5,819,723 A | 10/1998 | Joseph |
| 5,919,570 A * | 7/1999 | Hostettler ............. A61L 29/085 428/423.1 |
| 5,925,045 A | 7/1999 | Reimels et al. |
| 5,931,831 A * | 8/1999 | Linder ............. A61M 25/0026 604/264 |
| 5,993,413 A | 11/1999 | Aaltonen et al. |
| 6,022,214 A | 2/2000 | Hirsch et al. |
| 6,155,252 A | 12/2000 | Warters |
| 6,237,596 B1 | 5/2001 | Bohmfalk |
| 6,338,627 B2 | 1/2002 | Hirsch et al. |
| 6,374,827 B1 | 4/2002 | Bowden et al. |
| 6,398,775 B1 | 6/2002 | Perkins et al. |
| 6,460,540 B1 | 10/2002 | Klepper |
| 6,471,621 B2 | 10/2002 | Horstel et al. |
| 6,575,166 B2 | 6/2003 | Boussignac |
| 6,575,746 B2 | 6/2003 | Hirsch et al. |
| 6,604,528 B1 | 8/2003 | Duncan |
| 6,622,727 B2 | 9/2003 | Perry |
| 6,908,308 B2 | 6/2005 | Hirsch et al. |
| 6,935,340 B2 | 8/2005 | Saied |
| 6,974,321 B2 | 12/2005 | Hirsch et al. |
| 6,978,783 B2 | 12/2005 | Svendsen |
| 7,066,917 B2 | 6/2006 | Talamonti |
| 7,077,845 B2 | 7/2006 | Hacker et al. |
| 7,089,942 B1 | 8/2006 | Grey |
| 7,293,990 B2 | 11/2007 | Hirsch et al. |
| 7,465,847 B2 | 12/2008 | Fabian |
| 7,556,042 B2 | 7/2009 | West et al. |
| 7,578,814 B2 | 8/2009 | Accisano, III et al. |
| 7,833,188 B2 | 11/2010 | Gerber |
| 8,029,280 B2 | 10/2011 | Black et al. |
| 8,057,227 B2 | 11/2011 | Hirsch et al. |
| 8,057,228 B2 | 11/2011 | Hirsch et al. |
| 8,092,426 B2 | 1/2012 | Molnar |
| 8,092,427 B2 | 1/2012 | Urich et al. |
| 8,105,316 B2 | 1/2012 | Vadivelu |
| 8,122,889 B2 | 2/2012 | Vaska et al. |
| 8,122,890 B2 | 2/2012 | Vaska |
| 8,211,084 B2 | 7/2012 | Kassab et al. |
| 8,231,606 B2 | 7/2012 | Stenzler et al. |
| 8,292,620 B2 | 10/2012 | Black et al. |
| 8,297,973 B2 | 10/2012 | Hirsch et al. |
| 8,307,830 B2 | 11/2012 | Clayton |
| 8,414,544 B2 | 4/2013 | Resca |
| 2001/0008752 A1 | 7/2001 | Hirsch et al. |
| 2002/0039715 A1 | 4/2002 | Hirsch et al. |
| 2002/0103454 A1 | 8/2002 | Sackner et al. |
| 2002/0170556 A1 | 11/2002 | Gaitini |
| 2002/0179090 A1 | 12/2002 | Boussignac |
| 2003/0069553 A1 | 4/2003 | Talamonti |
| 2003/0106559 A1 | 6/2003 | Svendsen |
| 2003/0143512 A1 | 7/2003 | Hirsch et al. |
| 2003/0145862 A1 | 8/2003 | Perry |
| 2004/0000314 A1* | 1/2004 | Angel ................... A61M 16/04 128/207.14 |
| 2004/0079376 A1 | 4/2004 | Melker |
| 2004/0181251 A1 | 9/2004 | Hacker et al. |
| 2006/0037617 A1 | 2/2006 | Walke et al. |
| 2006/0084031 A1 | 4/2006 | Hirsch et al. |
| 2006/0260616 A1 | 11/2006 | West et al. |
| 2006/0260617 A1 | 11/2006 | Abolfathi et al. |
| 2007/0017527 A1* | 1/2007 | Totz ....................... A61M 16/04 128/207.15 |
| 2007/0032779 A1 | 2/2007 | Accisano, III et al. |
| 2007/0037120 A1 | 2/2007 | Ritter |
| 2007/0044806 A1* | 3/2007 | Madsen ............ A61M 16/0479 128/207.15 |
| 2007/0100300 A1 | 5/2007 | Hashemian |
| 2007/0225564 A1* | 9/2007 | Couvillon, Jr. ........ A61B 1/012 600/140 |
| 2008/0011304 A1* | 1/2008 | Stewart ................. A61M 16/04 128/207.15 |
| 2008/0086076 A1 | 4/2008 | Gerber |
| 2008/0114288 A1 | 5/2008 | Whayne et al. |
| 2008/0167603 A1 | 7/2008 | Stenzler et al. |

(56) References Cited

U.S. PATENT DOCUMENTS

| | | | |
|---|---|---|---|
| 2008/0171963 A1 | 7/2008 | Gerber | |
| 2008/0214947 A1 | 9/2008 | Hunt et al. | |
| 2008/0271741 A1 | 11/2008 | Graham et al. | |
| 2009/0101152 A1 | 4/2009 | Burk et al. | |
| 2009/0107497 A1 | 4/2009 | Stenzler et al. | |
| 2009/0120446 A1 | 5/2009 | Vaska et al. | |
| 2009/0246731 A1 | 10/2009 | Hirsch et al. | |
| 2009/0274991 A1 | 11/2009 | Black et al. | |
| 2009/0298012 A1 | 12/2009 | Hirsch et al. | |
| 2010/0087789 A1* | 4/2010 | Leeflang | A61B 17/3207 604/265 |
| 2010/0087798 A1 | 4/2010 | Adams et al. | |
| 2010/0094234 A1 | 4/2010 | Ramella et al. | |
| 2010/0119989 A1 | 5/2010 | Raybuck | |
| 2010/0288289 A1 | 11/2010 | Nasir | |
| 2010/0307507 A1 | 12/2010 | Li et al. | |
| 2011/0015611 A1 | 1/2011 | Gerber | |
| 2011/0022005 A1 | 1/2011 | Kocher | |
| 2011/0118659 A1 | 5/2011 | Maaskamp et al. | |
| 2011/0130744 A1 | 6/2011 | Kassab et al. | |
| 2011/0137267 A1* | 6/2011 | Phillips | A61M 25/0068 604/290 |
| 2011/0160683 A1 | 6/2011 | Pinotti Barbosa et al. | |
| 2011/0213336 A1 | 9/2011 | Cucin | |
| 2011/0311942 A1 | 12/2011 | Black et al. | |
| 2012/0006331 A1 | 1/2012 | Ward et al. | |
| 2012/0130327 A1 | 5/2012 | Marquez Canada | |
| 2012/0232472 A1 | 9/2012 | Bhagchandani et al. | |
| 2012/0259208 A1 | 10/2012 | Bloom et al. | |
| 2012/0279505 A1 | 11/2012 | Kim | |
| 2012/0310216 A1* | 12/2012 | Koltchine | A61B 5/01 604/528 |
| 2013/0019864 A1 | 1/2013 | Wondka | |
| 2013/0025607 A1 | 1/2013 | Altounian | |
| 2013/0125893 A1 | 5/2013 | Peace et al. | |

FOREIGN PATENT DOCUMENTS

| | | |
|---|---|---|
| EP | 0 578 376 | 1/1994 |
| EP | 0 589 577 | 3/1994 |
| EP | 0 595 499 | 5/1994 |
| EP | 0 599 472 | 6/1994 |
| EP | 0 651 974 | 5/1995 |
| EP | 0 888 792 | 1/1999 |
| EP | 2 305 343 | 4/2011 |
| GB | 242632 | 12/1925 |
| GB | 267828 | 3/1927 |
| GB | 270845 | 5/1927 |
| GB | 271721 | 6/1927 |
| GB | 271933 | 6/1927 |
| GB | 288740 | 4/1928 |
| GB | 289420 | 10/1928 |
| GB | 489407 | 7/1938 |
| WO | 1990/04992 | 5/1990 |
| WO | 1991/02554 | 3/1991 |
| WO | 1992/007602 | 5/1992 |
| WO | 1993/03777 | 3/1993 |
| WO | 1993/07917 | 4/1993 |
| WO | 1993/11819 | 6/1993 |
| WO | 1993/17742 | 9/1993 |
| WO | 1995/23624 | 9/1995 |
| WO | 1996/13217 | 5/1996 |
| WO | 1996/31248 | 10/1996 |
| WO | 1996/32895 | 10/1996 |
| WO | 1997/17034 | 5/1997 |
| WO | 1997/20584 | 6/1997 |
| WO | 1997/33635 | 9/1997 |
| WO | 1999/01170 | 1/1999 |
| WO | 1999/07428 | 2/1999 |
| WO | 1999/27840 | 6/1999 |
| WO | 1999/38548 | 8/1999 |
| WO | 2000/28916 | 5/2000 |
| WO | 2001/21129 | 3/2001 |
| WO | 2001/76659 | 10/2001 |
| WO | 2002/02160 | 1/2002 |
| WO | 2002/072185 | 9/2002 |
| WO | 2002/092144 | 11/2002 |
| WO | 2003/090813 | 11/2003 |
| WO | 2003/101516 | 12/2003 |
| WO | 2003/105941 | 12/2003 |
| WO | 2005/102458 | 11/2005 |
| WO | 2006/119557 | 11/2006 |
| WO | 2006/125006 | 11/2006 |
| WO | 2007/001342 | 1/2007 |
| WO | 2007/019074 | 2/2007 |
| WO | 2007/024230 | 3/2007 |
| WO | 2007/130579 | 11/2007 |
| WO | 2009/057055 | 5/2009 |
| WO | 2009/064914 | 5/2009 |
| WO | 2009/127028 | 10/2009 |
| WO | 2009/134295 | 11/2009 |
| WO | 2009/143045 | 11/2009 |
| WO | 2009/152104 | 12/2009 |
| WO | 2010/062603 | 6/2010 |
| WO | 2010/067225 | 6/2010 |
| WO | 2010/126586 | 11/2010 |
| WO | 2011/008758 | 1/2011 |
| WO | 2011/011743 | 1/2011 |
| WO | 2011/022802 | 3/2011 |
| WO | 2011/102674 | 8/2011 |
| WO | 2012/018362 | 2/2012 |
| WO | 2012/074978 | 6/2012 |
| WO | 2012/100100 | 7/2012 |
| WO | 2012/127436 | 9/2012 |
| WO | 2013/075060 | 5/2013 |
| WO | 2014/011932 | 1/2014 |
| WO | 2015/112835 | 7/2015 |

OTHER PUBLICATIONS

Jones, L. et al., "Silicone hydrogel contact lens materials update", Part 1, Jul. 2004 found at www.siliconehydrogels.org/editorials/index_july.asp and Part 2, Aug. 2004 found at www.siliconehydrogels.org/editorials/index_august.asp.

Benz Research & Development (BRD), "Advanced lens materials & manufacturing technology", 22 pages, (2012), found at http://benzrd.com/pdf/Advanced%20Lens%20Materials%2008.pdf.

Sole, M.L. et al., "Oropharyngeal secretion volume in intubated patients: the importance of oral suctioning", American Journal of Critical Care, vol. 20, No. 6, pp. 141-145, (2011).

International Search Report and Written Opinion dated Jul. 10, 2015 for PCT application No. PCT/US2015/012638, 12 pages.

Foroutan, H. et al., "Investigation of synthesis of PVP hydrogel by irradiation", Iranian Journal of Radiation Research, vol. 5, No. 3, pp. 131-136, (2007).

Wilcox, M.D.P., "Biocompatibility: Buzzword or breakthrough?", Review of Cornea & Contact Lenses, 4 pages, May 15, 2013 found at www.reviewofcontactlenses.com/content/c/40958.

Landers, R.A. et al., "Contact lens materials update: Options for most prescriptions", Contact Lens Spectrum, pp. 1-5, (2005), found at www.clspectrum.com/articleviewer.aspx?articleid=12768, printed on Jul. 30, 2015.

Snyder, C., "A primer on contact lens materials", Contact Lens Spectrum, vol. 19, No. 2, pp. 34-39, (2004).

Eye Health, "Contact Lens Materials & Water Content", AC Lens, found at www.aclens.com/lens-materials.asp, 2 pages, printed on Jul. 30, 2013.

"Types of contact lenses", British Contact Lens Association, 2 pages, printed on Jul. 30, 2013.

"Medical Devices, Types of Contact Lenses", U.S. Food and Drug Administration, 3 pages, found at www.fda.gov/medicaldevices/productsandmedicalprocedures/homehealthandconsumer/consumerproducts/contactlenses/ucm062319.htm, printed on Jul. 30, 2013.

"Advantages and disadvantages of various types of contact lenses", American Optometric Association, 3 pages, found at www.aoa.org/patients-and-public/caring-for-your-vision/contact-lenses/advantages-and-disadvantages-of-various-types-of-contact-lenses?sso=y, printed on Jul. 30, 2013.

(56) References Cited

OTHER PUBLICATIONS

"High performance materials", Benz Research & Development, 1 page, (2012), found at www.benzrd.com/clt_high_performance_materials.php, printed on Jul. 30, 2013.

* cited by examiner

ORAL SUCTION DEVICE

BACKGROUND

Endotracheal intubation is used to provide mechanical ventilation to patients who are unable to breath on their own. A tube is inserted into the trachea through the mouth to maintain an open airway, while a ventilator moves breathable gases in and out of the lungs. Mechanical ventilation requires keeping pressure in the lungs from the ventilator. An inflatable cuff connected to the endotracheal tube and positioned inside the trachea, seals the lungs and allows ventilation. The inflatable cuff also prevents oral secretions from reaching the lungs, when the glottis is kept open due to intubation. The inflatable cuff should provide the proper amount of pressure against the tracheal wall in order to effectively seal the lungs. If the pressure exerted by the inflated cuff is too high, the cuff may cause damage to the trachea. Insufficient pressure may result in insufficient sealing of the trachea, thus allowing aspiration of oral and gastric secretions into the lungs, with may result in ventilator-associated pneumonia. In practice, however, pressure sufficient to prevent all fluids from entering the lungs will cause damage to the trachea.

Oral secretions are produced by salivary glands, whose ducts open into the oral cavity. Salivary glands may produce approximately one liter of oral secretions per day. If oral secretions, potentially containing infectious bacteria, enter the lungs patients are exposed to the risk of contracting life-threatening infections, such as ventilator-associated pneumonia. Removal of oral secretions from intubated patients would reduce the risk of contracting ventilator-associated pneumonia.

Endotracheal tubes having lumen suction tubes for suctioning oral secretions are known. For example, International Application, International Publication Number WO 92/007602, describes an endotracheal tube, which provides gentle suction action to the tracheal wall. The endotracheal tube includes a main lumen, and an inflatable cuff connected to a cuff lumen for inflating and deflating the inflatable cuff. The endotracheal tube also includes a double lumen, which extends parallel inside the wall of the endotracheal tube and ends proximal to a suction eye, located proximal to the inflatable cuff. The double lumen includes a first lumen, and a second lumen, separated by a separation wall. In order to exercise gentle suction, the separating wall terminates approximately 5 mm from the beginning of the suction eye. However, if the cuff does not make a good seal, or when the cuff is deflated to remove the device from the patient's trachea, oral secretions present in the trachea may reach the lungs. Similar devices are described in German Patent No. DE 69126797, and International Applications, International Publication Numbers WO 95/23624, WO 99/38548, and WO 2010/067225.

SUMMARY

In a first aspect, the present invention is an oral suction device, comprising a suction catheter having a suction portion at a first end, a shell surrounding the suction portion, and a suction tubing connector on a second end opposite the first end. The shell comprises a hydrogel.

In a second aspect, the present invention is a method of removing fluids from a patient, comprising applying suction to the oral suction device of any of the preceding claims. The oral suction device is within the oral cavity of the patient.

In a third aspect, the present invention is an oral suction device, comprising a suction catheter having a suction portion, a sponge, a shell, a suction tubing connector on a first end of the suction catheter, an electronic temperature probe on a second end of the suction catheter opposite the suction tubing connector, an esophageal stethoscope comprising a stethoscope tube having a listening end, a seal separating the listening end of the esophageal stethoscope from the suction portion, a stethoscope connector on a first end of the stethoscope tube opposite the listening end, and one or more leads in electrical communication with the electronic temperature probe. The sponge is radiopaque and surrounds the suction portion. The shell comprises a hydrogel and surrounds the sponge and the suction portion. The stethoscope tube enters the suction catheter near the suction tubing connector and is located within the suction catheter.

DETAILED DESCRIPTION

A problem with using a suction device in a patient's mouth for an extended period of time is that contact between the device and the oral mucosa may cause abrasions and ulcerations in the patient's mouth. Furthermore, removal of oral secretions from the mouth or throat by suction may cause desiccation of the mouth or throat, leading to persistent cough, fungal infections, cavities, periodontitis and ulcers. It is desirable to avoid the onset of such conditions in an intubated patient. The present invention makes use of the discovery that an oral suction device that includes a hydrogel provides gentle contact with the mucosa and maintains the mouth and throat wet, thus avoiding mouth and throat ulcerations and dryness when the device is used on an intubated patient, and can prevent or inhibit the occurrence of ventilator-associated pneumonia. Furthermore, it has also been discovered that providing suction throughout the mouth (both front and back) and in the throat, provides efficient removal of oral secretions. Preferably, the oral suction device suctions away fluids in the oral cavity, the hypopharynx and the supraglotic regions. Since intermittent suction is always on and not dependent on an operator for timing of suction, it will avoid the build-up of fluids and is less expensive to operate. Since the oral suction device may be attached to the endotracheal tube, it is safely fixed in position and may be easily removed.

The oral suction device of the present invention includes a suction tubing connector, a suction catheter, and a shell. Optionally, the device may include a retention connector, a sponge, an esophageal stethoscope, and an electronic temperature probe. The oral suction device of the present invention is adapted for placement into a patient's mouth. The shell surrounds the suction portion of the suction catheter and is positioned within the oral cavity and oropharynx of the patient. Optionally, a sponge surrounds the suction portion of the suction catheter and the shell surrounds the sponge. Optionally, the device may include an esophageal stethoscope and/or electronic temperature probe, which is inserted in the patient's esophagus. Optionally, a connector may be included, which connects the oral suction device to an endotracheal tube.

Figure 1:
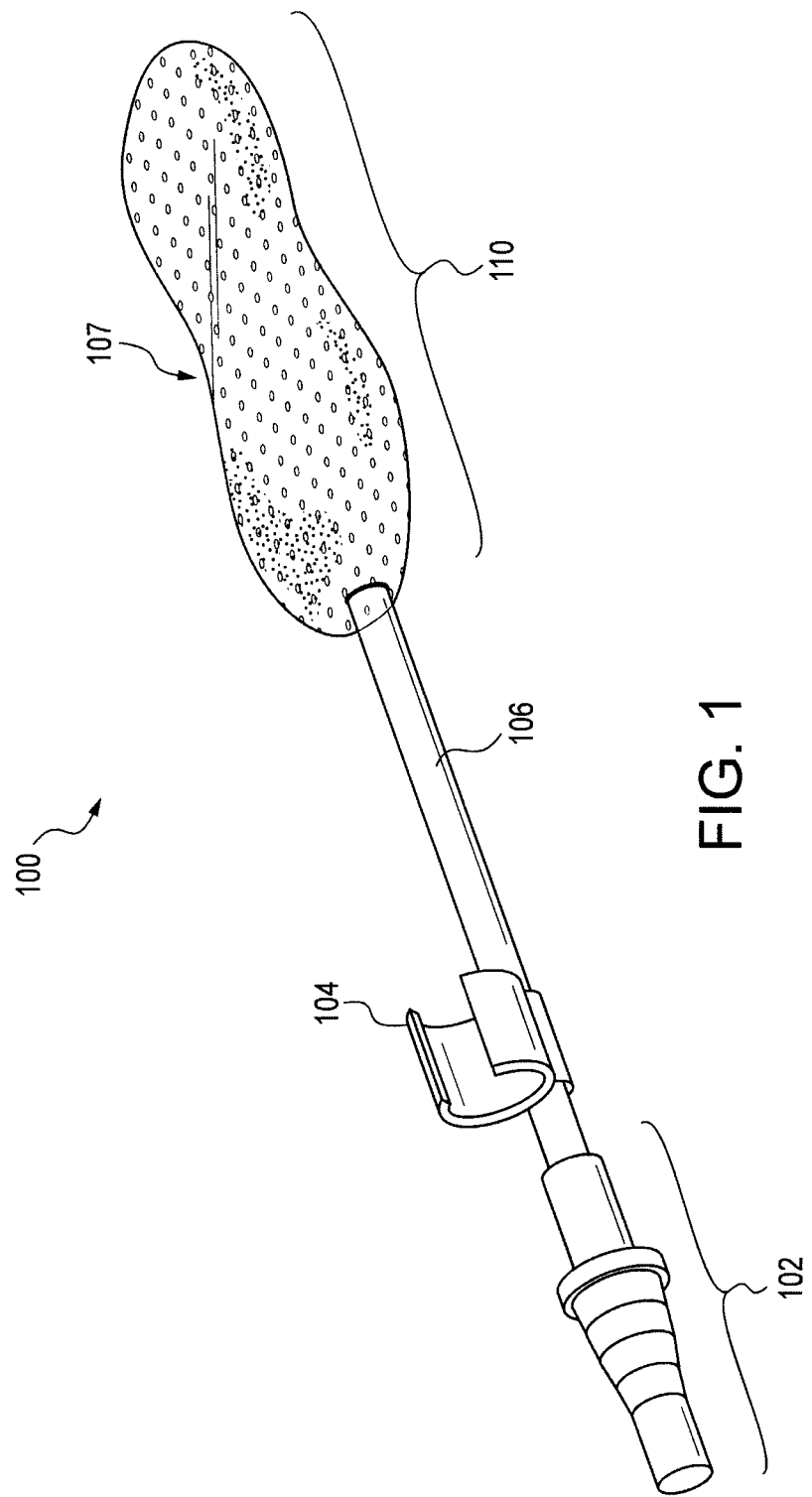
FIG. 1 is a plan view showing an oral suction device.

FIG. 1 illustrates an oral suction device 100. The oral suction device includes a suction tubing connector 102, which is connected to a suction catheter 106. The suction tubing connector may be connected to an external suction machine (not illustrated). Optionally, a retention connector 104 is connected to the suction catheter, for fixing the location of the oral suction device to an external device, such as an endotracheal tube. A suction end 110 of the oral suction device includes the suction portion (not shown) of the suction catheter 106. The suction end may be oval in shape, or may have an expanded figure-8 shape with a narrow portion 107 in the middle.

Figure 2:
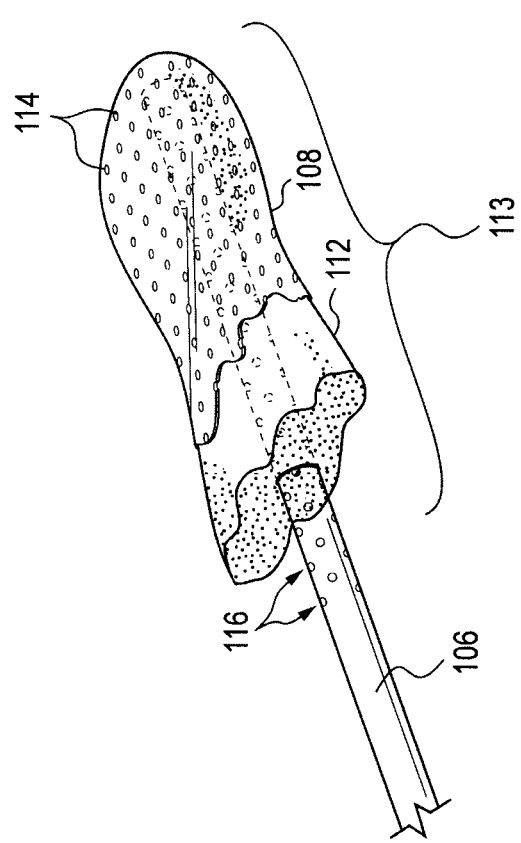
FIG. 2 is a cut away view of an oral suction device.

FIG. 2 illustrates a cut away view of the suction end of an oral suction device. The suction end of the oral suction device includes a shell 108 surrounding an optional sponge 112. The sponge surrounds the suction portion 113 of the suction catheter 106. When the optional sponge is absent, the shell may be thicker, taking the place of the sponge. The shell includes a plurality of holes 114 to allow rapid removal of fluids. The suction portion of the suction catheter also includes a plurality of holes 116, in fluid communication with the optional sponge and holes in the hydrogel, for suctioning fluids.

Figure 3:
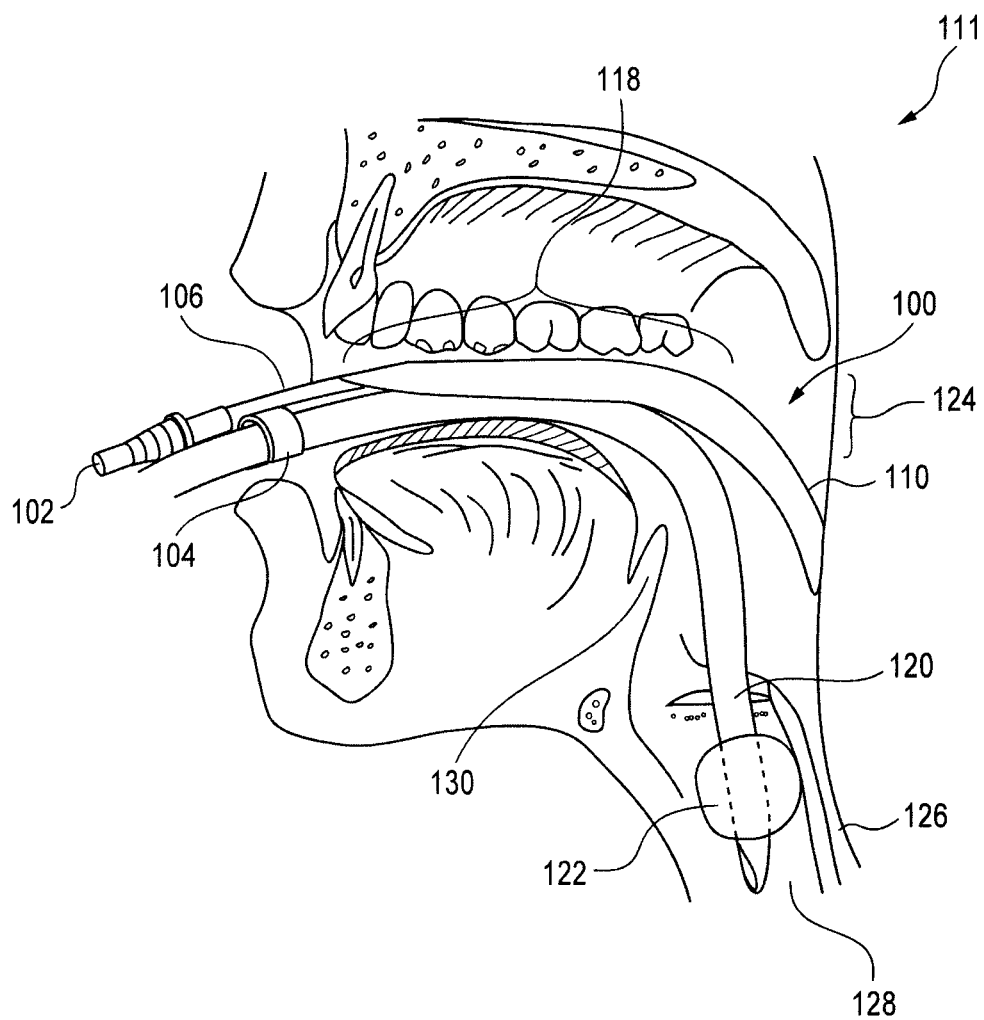
FIG. 3 is a dissection view showing a lateral aspect of a head and neck with an oral suction device.

FIG. 3 illustrates the positioning of the oral suction device 100 in a patient. The illustrations shows a cross section of a portion of a patient's head 111, with emphasis on the oral cavity 118, the oropharynx 124, and including the trachea 128, the esophagus 126 and the epiglottis 130; portions of the head and neck have been left out of the illustration for clarity. As shown, the patient is intubated with an endotracheal tube 120 having an inflated endotracheal cuff 122. The suction end 110 of the oral suction device extends from the front of the oral cavity, through the pharyngeal isthmus, into the oropharynx, and preferably makes contact with the back of the throat. The narrower section (107 in FIG. 1) of the suction end of the oral suction device will preferably be located at the pharyngeal isthmus. As illustrated, the retention connector 104 holds the oral suction device to the endotracheal tube. Once positioned within the patient, the suction tubing connector 102 may be connected to an intermittent suction device typically found in an intensive care unit (ICU) of a hospital, so that fluids, such oral secretions, nasal secretions and/or gastric fluids may be removed through the suction catheter 106. Preferably, the oral suction device suctions away fluids in the oral cavity, the hypopharynx and the supraglotic regions.

Suction catheters are flexible plastic tubes, which include an open hole on one (where they may be attached to the suction tubing connector) and on the opposite end a suction portion having a plurality of holes. Suction catheters including a suction tubing connector are commercially available, for example SAFE-T-VAC™ single suction catheters available from Abbey Medical (Fresno, Calif.), GENTLE FLO™ suction catheters by Covidien available from Health Products Express, Inc. (Boston, Mass.), and french suction catheter with depth markings (MEDLINE DYND 41902) available from Medline industries, Inc. (Mundelein, Ill.).

Preferably, the suction catheter has a length of 10 to 40 cm, more preferably 15 to 30 cm, including 16, 17, 18, 19, 20, 21, 22, 23, 24, 25, 26, 27, 28 and 29 cm. Preferably, the suction portion of the suction catheter has a length 0.25 to 0.75 percent of the length of the suction catheter, for example a length of 2.5 to 30 cm, or 4 to 22 cm, including 6, 7, 8, 9, 10, 11, 12, 13, 14, 15, 16, 17, 18, 19 and 20 cm. The number of holes present in the suction portion of the suction catheter is preferably, 6 to 100, more preferably 10 to 60, including 12, 16, 20, 24, 28, 32, 36, 40, 44, 48, 52 and 56 holes. The holes may form a regular pattern, or an irregular pattern. The diameter of the suction catheter is preferably 0.2 to 2 cm, more preferably 0.3 to 1.5 cm, including 0.4, 0.5, 0.6, 0.7, 0.8, 0.9 and 1.0 cm. Preferably, the suction portion of the suction catheter is surrounded by the shell, so that all liquids must pass through the shell during use of the oral suction device. The suction tubing connector is preferably 2 to 10 cm long, more preferably 3 to 8 cm long, including 4, 5, 6 and 7 cm long. The suction tubing connector makes a liquid tight and preferably air tight seal when connected to a suction catheter at an end opposite from the suction portion. The suction tubing connector is adapted to make a fluid tight seal with a flexible and elastic tubing connected to an intermittent suction device.

Preferably, the oral suction device is sterile. Preferably the suction catheter is sterile. Preferably, the sponge is sterile. Preferably, shell is sterile. Preferably, one or more of the suction catheter, the sponge and the shell are sterile.

Sponges may be cut to the desired size and shape from any surgical or nasal sponge, preferably radiopaque, for example DEROYAL® Surgical Sponges containing an X-ray detectable radiopaque element, available from DeRoyal (Powell, Tenn.). Another example is sponges described in U.S. Pat. No. 7,465,847. The sponge must be large enough to surround the suction portion of the suction catheter. Preferably, the sponge has a length of 3 to 35 cm, or 5 to 25 cm, including 6, 7, 8, 9, 10, 11, 12, 13, 14, 15, 16, 17, 18, 19, 20, 21, 22, 23 and 24 cm. The sponge may be oval in shape or may have an expanded figure-8 shape with a narrow portion in the center. Other shapes are also possible. At the widest point, the sponge has a width of preferably 2 to 8 cm, more preferably 3 to 7 cm, including 4, 5, and 6 cm. At the narrowest point, the sponge is preferably 2 to 8 cm, more preferably 3 to 7 cm, including 4, 5, and 6 cm. The height of the sponge is preferably 0.3 to 4 cm, more preferably 0.4 to 3.5 cm, including 0.5, 0.6, 0.7, 0.8, 0.9, 1.0, 1.2, 1.4, 1.5, 1.6, 1.8, 2.0, 2.5 and 3.0 cm high. The sizing of the sponge is based on the size after the suction catheter is placed inside it. Furthermore, the sponge may be monolithic, or may be composed of 2, 3, 4 or more separate sponges. Sponges with larger pores are preferred, for example 20 or 30 pores per inch.

Figure 4A:
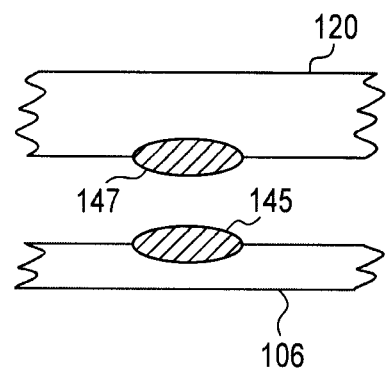
FIGS. 4A and 4B illustrate retention connectors.
Figure 4B:
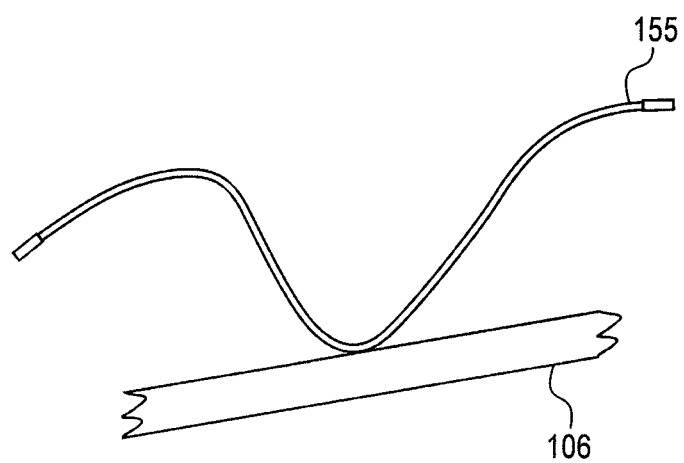

A retention connector may be a C-clip, made of metal or preferably plastic, as illustrated in FIG. 1. Alternatively, the retention connector may be a magnet 145 attached to the suction catheter 106, which mates by magnetic force to a similar magnet 147 attached to the endotracheal tube 120, as illustrated in FIG. 4A. In another alternative, the retention connector may be a string 155 attached to the suction catheter 106, as illustrated in FIG. 4B. The retention connector may be glued, for example with an adhesive, preferably a biocompatible adhesive such as LOCTITE® medical device adhesive, available from Henkel Corporation (Rocky Hill, Conn.), to the suction catheter; similarly the magnets 145 and 147 may be attached to the suction catheter and endotracheal tube, respectively, with an adhesive or biocompatible adhesive. Preferably, the oral suction device is attached to an endotracheal tube during use. In further alternative, the retention connector, such as the C-clip, may be formed as a integrated piece with the suction catheter, to form a monolithic structure.

The shell may be formed of a hydrogel material. The hydrogel materials contain a polymer, have a high water content, are soft, and are biocompatible (that is, they do not irritate mucosal tissue when in contact for long periods of time, for example 1 hour, 1 day or 1 week). Examples of hydrogel materials include polyacrylamide, agar-agar, polyvinyl pyrrolidone (PVP), silicone hydrogels, and hydrogels used in contact lenses (for example tefilcon, hioxyfilcon A, lidofilcon, omafilcon A, hefilcon C, phemfilcon, methafilcon A and ocufilcon D) and mixtures thereof. Other examples include polymers and co-polymers of 2-hydroxyethylmethacrylate, glyceryl methacrylate, methyl methacrylate, N-vinyl pyrrolidone, N-vinyl-2-pyrrolidone, 2-methacryloyloxyethyl phosphorylcholine, ethoxyethyl methacrylate and methacrylic acid. The hydrogel will also contain water, and may contain one or more salts such as sodium chloride, buffers, preservatives, plasticisers and polyethylene glycol. A preferred hydrogel is a mixture of PVP, polyethylene glycol, agar-agar and water; such a material is commercially available as SWISS THERAPY® Intensive Transdermal Eye Mask, manufactured by Kikgel (Sklodowskiej, Poland) and available from Invotec International, Inc. (Jacksonville, Fla.). Methods of making and materials for hydrogels are well known. See for example: Maldonado-Codina, C., "Hydrogel lenses—materials and manufacture: a review" *Optometry in Practice*, 4: 101-15 (2003); Jones et al., "Silicone hydrogel contact lens materials update" (July 2004), available online at www.siliconehydrogels.org/editorials/index_july.asp and www.siliconehydrogels.org/editorials/index_august.asp; and Benz Research & Development (BRD), "Advanced lens materials & manufacture technology", available online at www.benzrd.com/pdf/Advanced Lens Materials 08.pdf.

The shell and/or the optional sponge may be impregnated with one or more antibiotics. Examples of antibiotics include cephalosporines such as ceftriaxone, ceftazidime and cefepime; fluoroquinolones such as ciprofloxacin, levofloxacin and moxifloxacin; β-lactams such as ampicillin, sulbactam, piperacillin, tazobactam, ticarcillin, clavulanate and ureidopenicillin; carbapenems such as ertapenem, imipenem and meropenem; glycopeptides such as vancomycin; oxazolidinones such as linezolid; and aminoglycosides such as gentamicin, amikacin and tobramycin; and mixtures thereof. Alternatively, one or more of these antibodics, and mixtures thereof, may be administered as a liquid or spray into the patient's mouth, so that it will coat the oral cavity and/or the oropharynx, before being suctioned away by the oral suction device.

The shell must be large enough to surround the suction portion of the suction catheter, or if an optional sponge is present, surround the sponge. Furthermore, the shell may be fixed to the suction catheter or the optional sponge simply by being wrapped around it, or by an adhesive, preferably a biocompatible adhesive such as LOCTITE® medical device adhesive, available from Henkel Corporation (Rocky Hill, Conn.). Preferably, the shell has a length of 3 to 35 cm, or 5 to 25 cm, including 6, 7, 8, 9, 10, 11, 12, 13, 14, 15, 16, 17, 18, 19, 20, 21, 22, 23 and 24 cm. The shell may be oval in shape or may have an expanded figure-8 shape with a narrow portion in the center (as illustrated in FIG. 1). Other shapes are also possible. At the widest point, the shell has a width of preferably 2 to 8 cm, more preferably 3 to 7 cm, including 4, 5, and 6 cm. At the narrowest point, the shell is preferably 2 to 8 cm, more preferably 3 to 7 cm, including 4, 5, and 6 cm. The height of the shell is preferably 0.3 to 4 cm, more preferably 0.4 to 3.5 cm, including 0.5, 0.6, 0.7, 0.8, 0.9, 1.0, 1.2, 1.4, 1.5, 1.6, 1.8, 2.0, 2.5 and 3.0 cm high. The sizing of the shell is based on the size after the suction catheter is placed inside it, or when a sponge is present, after the sponge is inside it. When a sponge is used, the shell may preferably have a thickness of 0.01 to 3 cm, more preferably 0.05 to 2 cm, including 0.1, 0.2, 0.3, 0.4, 0.5, 0.6, 0.7, 0.8, 0.9 and 1 cm. The shell contains a plurality of holes. The number of holes present in the shell is preferably 10 to 10,000, more preferably 100 to 1000.

Figure 5:
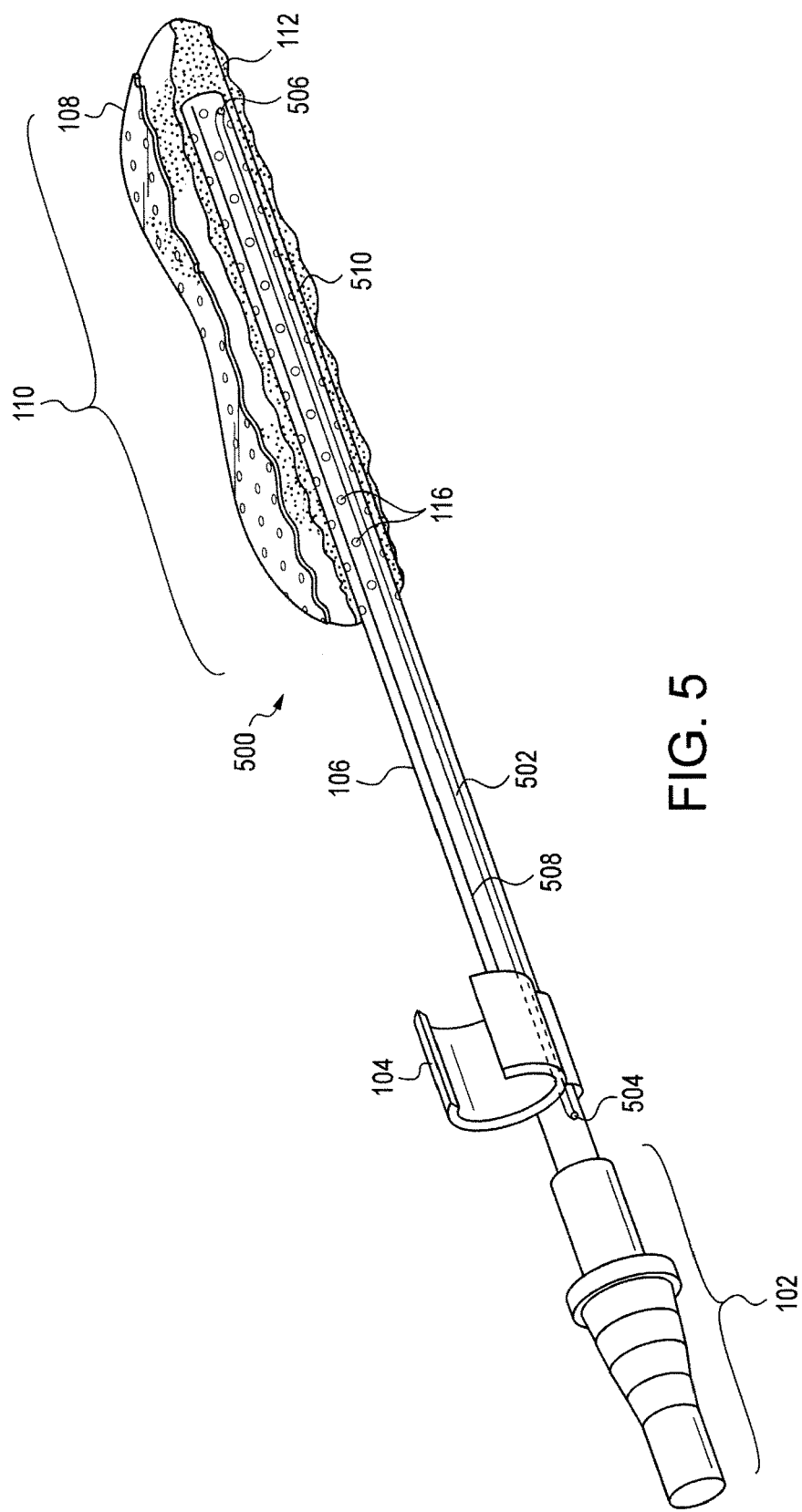
FIG. 5 shows an oral suction device including a vacuum lock relief tube.

FIG. 5 illustrates an oral suction device 500 including a vacuum lock relief tube; the suction end 110 of the oral suction device 500 is illustrated as a cut-away to show details of the interior of the suction end. The oral suction device includes suction catheter 106 connected to a suction tubing connector 102, and a retention connector 104 connected to the suction catheter. The suction portion of the suction catheter, including holes 116 is surrounded by an optional sponge 112, and surrounded by a shell 108. Also present is a vacuum lock relief tube 502, inside the suction catheter, which extends from suction end of the suction catheter, to a point between the suction end of the suction catheter and the retention connector. A first end 504 of the vacuum lock relief tube exits through the wall of the suction catheter, and a second end 506 of the vacuum lock relief tube also exits through the wall of the suction catheter, from within the suction end of the oral suction device. In this way the vacuum lock relief tube creates a gas pathway between the atmosphere and the inside of the sponge or shell. If some of the holes in the suction portion of the suction catheter are blocked, for example by thick mucus, the amount of suction pulling through the remaining holes and the holes in the shell nearby may be great enough to hold tissue from inside the patient's oral cavity or oropharynx tightly against the oral suction device, creating a "vacuum lock" blocking the flow of fluids into the oral suction device. The vacuum lock relief tube prevents the creating of a vacuum lock, by allowing atmospheric air from outside the patient's mouth to enter into the sponge and shell. As illustrated an optional radiopaque element 508 is present in the suction catheter, and an optional radiopaque element 510 is present in the sponge. The radiopaque element may optionally be present in all embodiments.

Figure 6:
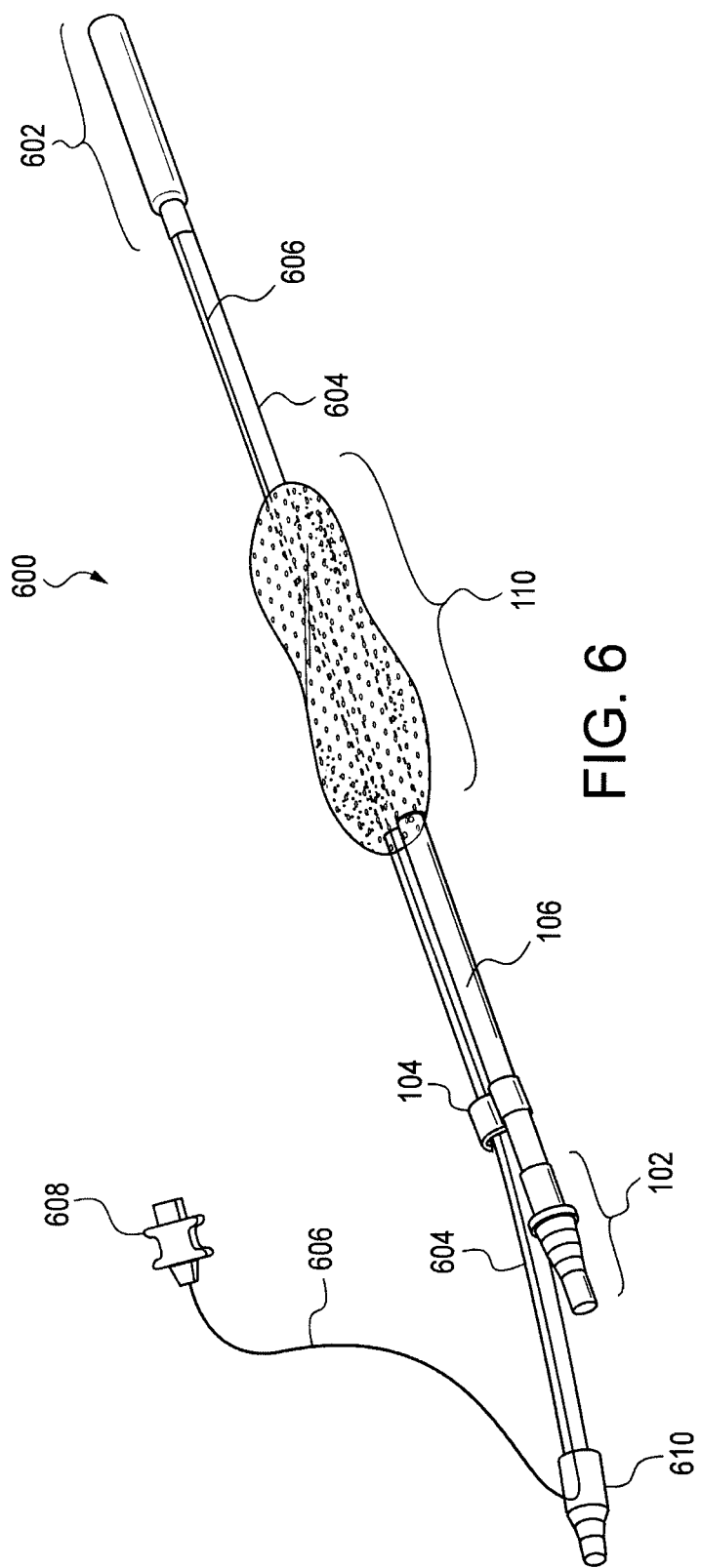
FIG. 6 shows an oral suction device including an esophageal stethoscope and electronic temperature probe.

FIG. 6 illustrates an oral suction device 600 including an esophageal stethoscope and an electronic temperature probe. The oral suction device includes a suction catheter 106 connected to a suction tubing connector 102, and a retention connector 104 connected to the suction catheter, while the suction portion (not illustrated) of the suction catheter is inside the suction end 110 of the oral suction device. An electronic temperature probe 602 is located at a first end of a lead tube 604 which passes through the suction end of the oral suction device, approximately parallel to the suction catheter. Leads 606, which electrically connect the electronic temperature probe with a monitoring device (not illustrated), pass through the lead tube, and may exit the lead tube through an optional lead seal 610. The ends of the leads may be connected to an optional lead adaptor 608, which is adapted for mating with a complementary socket on a monitoring device, for completing the electrical connections between the electronic temperature probe and the monitoring device. The lead tube functions as the esophageal stethoscope and transmits heart and respiratory sounds for auscultation.

The optional esophageal stethoscope and electronic temperature probe may be connected to the suction catheter via the retention connector located on the lead tube. The esophageal stethoscope and electronic temperature probe may be placed in the patient's mouth with the distal tip positioned just above the gastroesophageal junction in the distal portion of the esophagus. The esophageal stethoscope allows auscultation of a patient's heart tones, rates and rhythms, and the electronic temperature probe allows monitoring the patient's core temperature. An example of an esophageal stethoscope and electronic temperature probe is the LIFE-SOUND™ esophageal stethoscope available from NOVAMED USA (Elmsford, N.Y.).

Figure 7A:
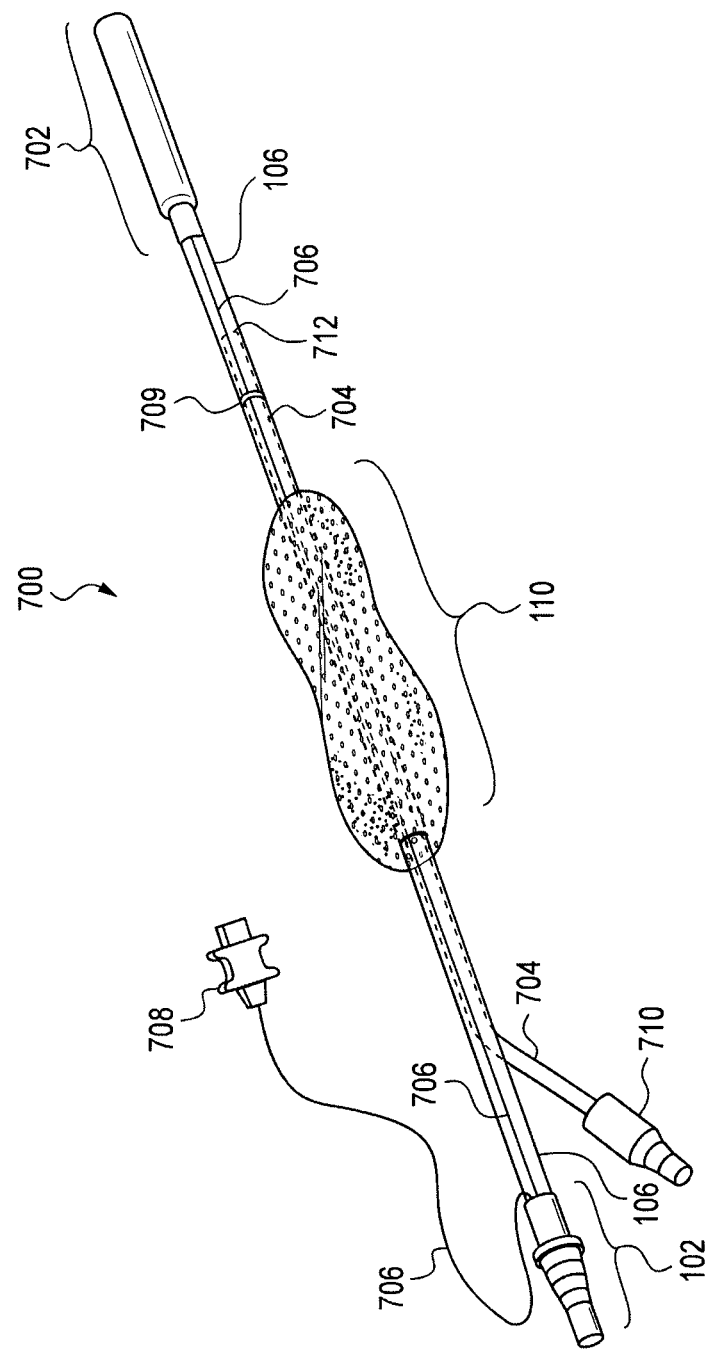
FIG. 7A shows an alternative oral suction device including an esophageal stethoscope and electronic temperature probe.

FIG. 7A illustrates an alternative oral suction device 700 including an esophageal stethoscope and an electronic temperature probe. The oral suction device includes a suction catheter 106 connected to a suction tubing connector 102, while the suction portion (not illustrated) of the suction catheter is inside the suction end 110 of the oral suction device. An electronic temperature probe 702 is located at the opposite end of the suction catheter from the suction tubing connector. Leads 706, which electrically connect the electronic temperature probe with a monitoring device (not illustrated) pass through the suction catheter and may exit the suction catheter at the suction tubing connector. The ends of the leads may be connected to an optional lead adaptor 708, which is adapted for mating with a complementary socket on the monitoring device, for completing the electrical connections between the electronic temperature probe and the monitoring device. An esophageal stethoscope includes a stethoscope tube 704 with an isolated listening end 712. The stethoscope tube is connected to a stethoscope connector 710 and enters the suction catheter near the suction tubing connector. The stethoscope tube is located within the suction catheter with the listening end located between the suction end of the suction catheter and the electronic temperature probe. The listening end of the stethoscope is isolated from the suction by a stethoscope seal 709, which improves auscultation by reducing background noise caused by the suction. The stethoscope seal may be formed using a biocompatible sealant such as LOCTITE® medical device adhesive.

In the alternative oral suction device shown in FIG. 7A, the diameter of the stethoscope tube must be smaller than the diameter of the suction catheter. Preferably, the diameter of the stethoscope tube is about half the diameter of the suction catheter. For example, the suction catheter may have a diameter of 6 mm (18 French) and the stethoscope tube may have a diameter of 3 mm (9 French). This design is particularly useful for anesthesiology use.

Figure 7B:
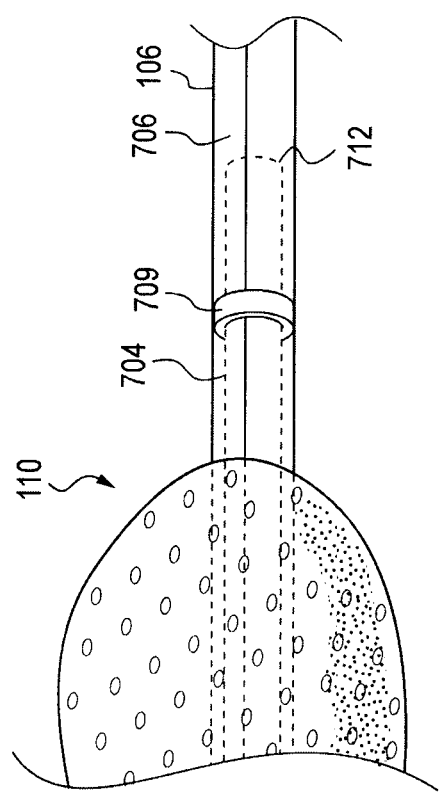
FIG. 7B shows a close up of the alternative oral suction device including an esophageal stethoscope and electronic temperature probe shown in FIG. 7A.

FIG. 7B illustrates a close up view of the listening end 712 of the esophageal stethoscope illustrated in FIG. 7A. The stethoscope seal 709 surrounds the stethoscope tube 704 to isolate the listening end of the esophageal stethoscope from the suction. The stethoscope seal may be located at any point along the stethoscope tube between the suction end 110 (partially illustrated) and the electronic temperature probe (not illustrated) to vary the length of the listening end. Leads 706 pass through the stethoscope seal but do not interfere with the noise isolation provided by the stethoscope seal. The stethoscope tube, leads, and stethoscope seal are all located within the suction catheter 106.

The oral suction device may be used on a patient under general anesthesia in a hospital's ICU. The oral suction device may be used on a patient undergoing surgery, or may be used on a patient post-surgery. The oral suction device may also be used, for example, on a trauma patient at the location where the trauma occurred, after the patient has been partially or fully sedated. If used on a patient who is not under general anesthesia, it may be desirable to apply a local anesthetic to the patient's throat before inserting the oral suction device.

In use, the suction end of the oral suction device is inserted in the patient's oral cavity, as illustrated in FIG. 3. The suction tubing connector is then connected to a suction device, preferably an intermittent suction device (such as the PUSH-TO-SET™ Digital Intermittent Suction Unit available from Ohio Medical Corporation (Gurnee, Ill.)), via a flexible elastic tubing. The oral suction device may then be connected to an endotracheal tube with the retention connector. The oral suction device will then remove fluids, during periods of suction, such as oral secretions, nasal secretions and/or gastric fluids, to prevent or inhibit ventilator-associate pneumonia. Medically trained personnel may determine the interval between suctioning and the duration of suctioning needed. Intermittent suctioning avoids the need of an operator, for example a nurse, to be present when suctioning is needed.

EXAMPLES

Intubated Patient in ICU (Prophetic Example)

Patient #1, age 72, suffering chronic obstructive pulmonary disease (COPD) is hospitalized and taken to the ICU, where the patient is administered general anesthesia and is intubated. After the patient has been sedated, medical personnel introduce an endotracheal tube through the patient's mouth and into the trachea. The cuff connected to the endotracheal tube is inflated to avoid gases from the ventilator escaping from the lungs and refluxing into the trachea. The endotracheal tube is connected to a ventilator. An oral suction device is introduced through the patient's mouth, positioning the suction portion such that half is in the patient's oral cavity and the other half in the patient's oropharynx. The oral suction device is connected to the endotracheal tube via the retention connector. Correct positioning of the oral suction device is confirmed by X-ray imaging of the patient's head, as the oral suction device includes a radiopaque sponge. The oral suction device is connected to an external device which provides intermittent suction. After three weeks, the patient's condition has been stabilized and the oral suction device and the endotracheal tube are removed. The patient is released and does not develop ventilator-associated pneumonia.

Intubated Patient Under Anesthesia (Prophetic Example)

Patient #2, age 32, is hospitalized and taken to the operating room for surgery, where the patient is administered general anesthesia and is intubated. After the patient has been sedated, medical personnel introduce an endotracheal tube through the patient's mouth and into the trachea. The cuff connected to the endotracheal tube is inflated to avoid gases from the ventilator escaping from the lungs and refluxing into the trachea. The endotracheal tube is connected to a ventilator. An oral suction device with an esophageal stethoscope and an electronic temperature probe is introduced through the patient's mouth, positioning the suction portion such that half is in the patient's oral cavity and the other half in the patient's oropharynx, and positioning the electronic temperature probe such that the distal tip is just above the gastroesophageal junction in the distal portion of the esophagus. The suction catheter of the oral suction device is an 18 French tube. The stethoscope tube is located within the suction catheter and is a 9 French tube. The listening end of the stethoscope is isolated from the suction by a stethoscope seal so that the suction noises do not interfere with monitoring the patient's heart sounds. The oral suction device is connected to the endotracheal tube via the retention connector. An earpiece is connected to the stethoscope connector, and hearing the patient's heart tones confirms correct placement of the electronic temperature probe. The oral suction device is connected to an external device which provides intermittent suction. The leads for the electronic temperature probe exit the suction catheter near the retention connector and are connected to a lead adapter, which connects the electronic temperature probe to a monitoring device. During the surgery, the patient's heart tones, heart rates, and heart rhythms are monitored through the esophageal stethoscope without interference from the suction. The patient's core temperature is monitored by the electronic temperature probe. After the surgery is complete, the oral suction device with the esophageal stethoscope and the electronic temperature probe and the endotracheal tube are removed. The patient is transferred to a recovery room and later released from the hospital. The patient does not develop ventilator-associated pneumonia.

REFERENCES

1. Sole, M. L., et al., "Oropharyngeal secretion volume in intubated patients: the importance of oral suctioning", *Am J Crit Care,* 20(6):141-45 (2011).
2. International Application, International Publication Number WO 92/007602.
3. German Patent No. DE 69126797.
4. International Applications, International Publication Number WO 95/23624.
5. International Applications, International Publication Number WO 99/38548.
6. International Applications, International Publication Number WO 2010/067225.
7. U.S. Pat. No. 7,465,847.
8. Maldonado-Codina, C., "Hydrogel lenses—materials and manufacture: a review" *Optometry in Practice,* 4: 101-15 (2003).
9. Jones et al., "Silicone hydrogel contact lens materials update" (July 2004), available online at www.siliconehydrogels.org/editorials/index_july.asp and www.silicone-hydrogels.org/editorials/index_august.asp.
10. Benz Research & Development (BRD), "Advanced lens materials & manufacture technology", available online at www.benzrd.com/pdf/Advanced Lens Materials 08.pdf.

What is claimed is:

1. An oral suction device, comprising:
   a suction catheter having a suction portion at a first end,
   a shell surrounding the suction portion, and
   a suction tubing connector, on a second end opposite the first end,
   wherein the shell comprises a hydrogel,
   the suction portion of the suction catheter comprises a plurality of holes,
   the shell comprises a plurality of holes, and
   the plurality of holes in the shell are configured to, in use, allow removal therethrough of fluid from an oral cavity of a patient, the oral suction device further comprising a sponge surrounding the suction portion, wherein the shell surrounds the sponge.
2. The oral suction device of claim 1, wherein the sponge is radiopaque.
3. The oral suction device of claim 1, wherein the hydrogel comprises a polymer, water and a salt.
4. The oral suction device of claim 3, wherein the salt is sodium chloride.
5. The oral suction device of claim 1, wherein the suction portion has a length of 2.5 to 30 cm.
6. The oral suction device of claim 1, wherein the oral suction device is sterile.
7. The oral suction device of claim 1, further comprising a retention connector attached to the suction catheter.
8. The oral suction device of claim 7, wherein the retention connector is a C-clip.
9. The oral suction device of claim 1, wherein the hydrogel comprises at least one member selected from the group consisting of polyacrylamide; agar-agar; polyvinyl pryrrolidone; silicone hydrogels; and polymers and copolymers of 2-hydroxyethylmethacrylate, glyceryl methacrylate, methyl methacrylate, N-vinyl pyrrolidone, N-vinyl-2-pyrrolidone, 2-methacryloyloxyethyl phosphorylcholine, ethoxyethyl methacrylate and methacrylic acid.
10. The oral suction device of claim 1, wherein the hydrogel comprises polyvinyl pyrrolidone, polyethylene glycol, agar-agar and water.
11. The oral suction device of claim 1, wherein the hydrogel is impregnated with an antibiotic.
12. The oral suction device of claim 11, wherein the antibiotic is at least one member selected from the group consisting of cephalosporines, fluoroquinolones, β-lactams, carbapenems, glycopeptides and aminoglycosides.
13. The oral suction device of claim 1, wherein the shell has an expanded figure-8 shape.
14. The oral suction device of claim 1, further comprising an esophageal stethoscope and an electronic temperature probe.
15. The oral suction device of claim 14, further comprising a lead tube, wherein one or more leads located within the lead tube are in electrical communication with the electronic temperature probe.
16. The oral suction device of claim 15, wherein the one or more leads are connected to a lead adaptor.
17. The oral suction device of claim 1, wherein the shell has a length of 5 to 25 cm, a width at a widest point of 3 to 8 cm, a width at a narrowest point of 2 to 7 cm, and a height of 0.3 to 4 cm.
18. The oral suction device of claim 1, further comprising a vacuum lock relief tube inside the suction catheter, wherein the vacuum lock relief tube creates a gas pathway from atmosphere outside the suction catheter into the sponge or shell.
19. A method of removing fluids from a patient, comprising applying suction to the oral suction device of claim 1, wherein the oral suction device is within the oral cavity of the patient.
20. The oral suction device of claim 1, further comprising an esophageal stethoscope and an electronic temperature probe, wherein the esophageal stethoscope comprises a stethoscope tube having a listening end.
21. The oral suction device of claim 20, wherein the stethoscope tube is located within the suction catheter.
22. The oral suction device of claim 20, wherein a seal separates the listening end of the esophageal stethoscope from the suction portion.
23. The oral suction device of claim 1, wherein the hydrogel comprises a silicone hydrogel.
24. The oral suction device of claim 1, wherein the plurality of holes in the suction portion of the suction catheter is 6 to 100 holes, and the plurality of holes in the shell is 10 to 10,000 holes.

25. An oral suction device, comprising:
a suction catheter having a suction portion,
a sponge, surrounding the suction portion, wherein the sponge is radiopaque,
a shell comprising a hydrogel, surrounding the sponge and the suction portion,
a suction tubing connector on a first end of the suction catheter,
an electronic temperature probe on a second end of the suction catheter opposite the suction tubing connector,
an esophageal stethoscope comprising a stethoscope tube having a listening end, wherein the stethoscope tube enters the suction catheter near the suction tubing connector and is located within the suction catheter,
a seal, separating the listening end of the esophageal stethoscope from the suction portion,
a stethoscope connector on a first end of the stethoscope tube opposite the listening end, and
one or more leads in electrical communication with the electronic temperature probe.

* * * * *